United States Patent
Yamamoto et al.

(10) Patent No.: US 10,039,911 B2
(45) Date of Patent: Aug. 7, 2018

(54) APPLICATOR

(71) Applicant: HISAMITSU PHARMACEUTICAL CO., INC., Tosu-shi, Saga (JP)

(72) Inventors: Naoki Yamamoto, Tsukuba (JP); Makoto Ogura, Tsukuba (JP)

(73) Assignee: HISAMITSU PHARMACEUTICAL CO., INC., Tosu-shi, Saga (JP)

( * ) Notice: Subject to any disclaimer, the term of this patent is extended or adjusted under 35 U.S.C. 154(b) by 0 days.

(21) Appl. No.: 14/899,148

(22) PCT Filed: Jun. 17, 2014

(86) PCT No.: PCT/JP2014/066068
§ 371 (c)(1),
(2) Date: Dec. 17, 2015

(87) PCT Pub. No.: WO2014/203910
PCT Pub. Date: Dec. 24, 2014

(65) Prior Publication Data
US 2016/0144160 A1 May 26, 2016

(30) Foreign Application Priority Data

Jun. 19, 2013 (JP) ................................. 2013-128624

(51) Int. Cl.
*A61M 5/00* (2006.01)
*A61M 37/00* (2006.01)

(52) U.S. Cl.
CPC . *A61M 37/0015* (2013.01); *A61M 2037/0023* (2013.01)

(58) Field of Classification Search
CPC ...... A61M 37/0015; A61M 2037/0023; A61M 2037/0046; A61M 2037/0061

USPC .......................................................... 604/173
See application file for complete search history.

(56) References Cited

U.S. PATENT DOCUMENTS

| | | | |
|---|---|---|---|
| 6,589,202 B1 | 7/2003 | Powell | |
| 2002/0091357 A1* | 7/2002 | Trautman | A61B 17/205 604/117 |
| 2003/0083645 A1 | 5/2003 | Angel et al. | |
| 2004/0087992 A1 | 5/2004 | Gartstein et al. | |
| 2005/0112135 A1 | 5/2005 | Cormier et al. | |

(Continued)

FOREIGN PATENT DOCUMENTS

| | | |
|---|---|---|
| AU | 2012200649 A1 | 2/2012 |
| EP | 1360935 A1 | 11/2003 |

(Continued)

OTHER PUBLICATIONS

International Preliminary Report on Patentability for WO Patent Application No. PCT/JP2014/066068 dated Dec. 30, 2015.

(Continued)

*Primary Examiner* — Phillip Gray
(74) *Attorney, Agent, or Firm* — Nath, Goldberg & Meyer; Tanya E. Harkins; Joshua B. Goldberg

(57) ABSTRACT

An applicator of one aspect for applying microneedles to skin includes a resistive portion configured to apply resistance against movement of a microneedle sheet having the plurality of microneedles formed along a main surface of the sheet, and a bending portion configured to bend the microneedle sheet passed through the resistive portion to raise the microneedle from the main surface.

9 Claims, 21 Drawing Sheets

(56) References Cited

U.S. PATENT DOCUMENTS

| | | |
|---|---|---|
| 2005/0245845 A1 | 11/2005 | Roe et al. |
| 2006/0149297 A1 | 7/2006 | Sherman et al. |
| 2007/0106207 A1 | 5/2007 | Withey |
| 2008/0125743 A1 | 5/2008 | Yuzhakov |
| 2010/0168638 A1 | 7/2010 | Korogi et al. |
| 2010/0262081 A1 | 10/2010 | Lee et al. |

FOREIGN PATENT DOCUMENTS

| | | | | |
|---|---|---|---|---|
| GB | 2448493 A | * | 10/2008 | ........ A61M 37/0015 |
| GB | 2480542 A | | 11/2011 | |
| JP | 3016317 U | | 7/1995 | |
| JP | 3049583 U | | 4/1998 | |
| JP | H10290820 A | | 11/1998 | |
| JP | 2001061894 A | | 3/2001 | |
| JP | 2004501726 A | | 1/2004 | |
| JP | 2005503210 A | | 2/2005 | |
| JP | 2008543528 A | | 12/2008 | |
| JP | 2017-820 A | | 1/2017 | |
| KR | 1020110092914 A | | 8/2011 | |
| WO | 0202177 A1 | | 1/2002 | |
| WO | 2007/002522 A1 | | 1/2007 | |
| WO | 2008091878 A1 | | 7/2008 | |
| WO | 2012144437 A1 | | 10/2012 | |
| WO | 2013038890 A1 | | 3/2013 | |
| WO | 2013187392 A1 | | 12/2013 | |
| WO | 2014203911 A1 | | 12/2014 | |

OTHER PUBLICATIONS

International Preliminary Report on Patentability for WO Patent Application No. PCT/JP2014/066070 dated Dec. 30, 2015.
ISR for WO Patent Application No. PCT/JP2014/066070 dated Sep. 22, 2014.
International Search Report dated Sep. 22, 2014 corresponding to International application No. PCT/JP2014/066068.
European Search Report dated Feb. 15, 2017 in corresponding to European Patent Counterpart Application No. 4813654.2.
European Search Report dated Feb. 7,2017 issued in corresponding European Application No. EP14814482.7.
Office Action dated Apr. 3, 2017 in connection with not Counterpart U.S. Appl. No. 14/407,258.
Office Action dated Apr. 7, 2017 in connection with not Counterpart U.S. Appl. No. 14/916,354.
Office Action dated May 19, 2017 in connection with Counterpart Chinese Patent Application No. 201480034452.X.
Notice of Allowance dated May 31, 2017 in connection with Counterpart Korean Patent Application No. 10-2016-7000284.
European Search Report dated Mar. 28, 2017 in corresponding European Patent Application No. 14843133.1.

* cited by examiner

APPLICATOR

This is a National Phase Application filed under 35 U.S.C. 371 as a national stage of international application no. PCT/JP2014/066068, filed Jun. 17, 2014, an application claiming the benefit of Japanese application no. 2013-128624, filed Jun. 19, 2013, the content of each of which is hereby incorporated by reference in its entirety.

TECHNICAL FIELD

An aspect of the present invention relates to an applicator used for assisting in administration of an active component by microneedles.

BACKGROUND ART

Microneedles for administrating active components through skin and devices including the microneedles are conventionally known. For example, a rotatable microstructure apparatus disclosed in Patent Literature 1 below includes a curved substrate and a roller structure including a plurality of microelements affixed upon a first surface of the substrate. The microelements are of predetermined sizes and shapes so as to penetrate a stratum corneum layer of skin when the microstructure apparatus is placed upon the skin and rolled over the skin in a predetermined direction.

CITATION LIST

Patent Literature

[Patent Literature 1] Japanese Unexamined Patent Publication No. 2005-503210

SUMMARY OF INVENTION

Technical Problem

Unfortunately, in the microstructure apparatus disclosed in Patent Literature 1, the force exerted in the skin depth direction varies with users because the microelements are inserted by rolling the roller mounted on the arm by human hand. The direction of force exerted on the microelements is therefore unstable, which leads to large variations in insertion. The reproducibility of puncture is thus not guaranteed. It is therefore desired to minimize variations in procedure to increase the reproducibility of puncture.

Solution to Problem

According to an aspect of the present invention, an applicator for applying microneedles to skin is provided. The applicator includes a resistive portion configured to apply resistance against movement of a microneedle sheet having the plurality of microneedles formed along a main surface of the sheet, and a bending portion configured to bend the microneedle sheet passed through the resistive portion to raise the microneedles from the main surface.

In such an aspect, resistance acts against the movement of the microneedle sheet, and the bending portion raises the microneedles. The microneedles can be inserted into skin with almost no force applied in directions other than the horizontal direction and in a constant direction of the force exerted. That is, the reproducibility of puncture can be increased.

In the applicator according to another aspect, the resistive portion may be a first cylindrical member configured to change the direction of movement of the microneedle sheet.

In the applicator according to another aspect, the first cylindrical member may reverse the direction of movement of the microneedle sheet.

In the applicator according to another aspect, the bending portion may be a second cylindrical member configured to bend the microneedle sheet by changing the direction of movement of the microneedle sheet.

In the applicator according to another aspect, the second cylindrical member may reverse the direction of movement of the microneedle sheet.

The applicator according to another aspect may further include a slider configured to slide the second cylindrical member such that the second cylindrical member moves away from the first cylindrical member.

The applicator according to another aspect may further include a slider configured to slide the first and second cylindrical members simultaneously.

In the applicator according to another aspect, the resistive portion may sandwich the microneedle sheet to apply resistance to the microneedle sheet.

In the applicator according to another aspect, the resistive portion may be a tubular structure wrapped with the microneedle sheet to feed the microneedle sheet toward the bending portion.

Advantageous Effects of Invention

According to an aspect of the present invention, the reproducibility of puncture can be increased.

DESCRIPTION OF EMBODIMENTS

Embodiments of the present invention will be described in details below with reference to the accompanying drawings.

In the description of the drawings, the same or equivalent components are denoted with the same reference signs and an overlapping description will be omitted.

First Embodiment

An applicator 10 according to a first embodiment is an assist device for inserting microneedles on a microneedle sheet 20 into skin for administering any given active component (for example, drugs) into a living body. The user can use this applicator 10 to insert the microneedles into skin with more appropriate force than when bending the microneedle sheet 20 directly by hand.

Figure 1:
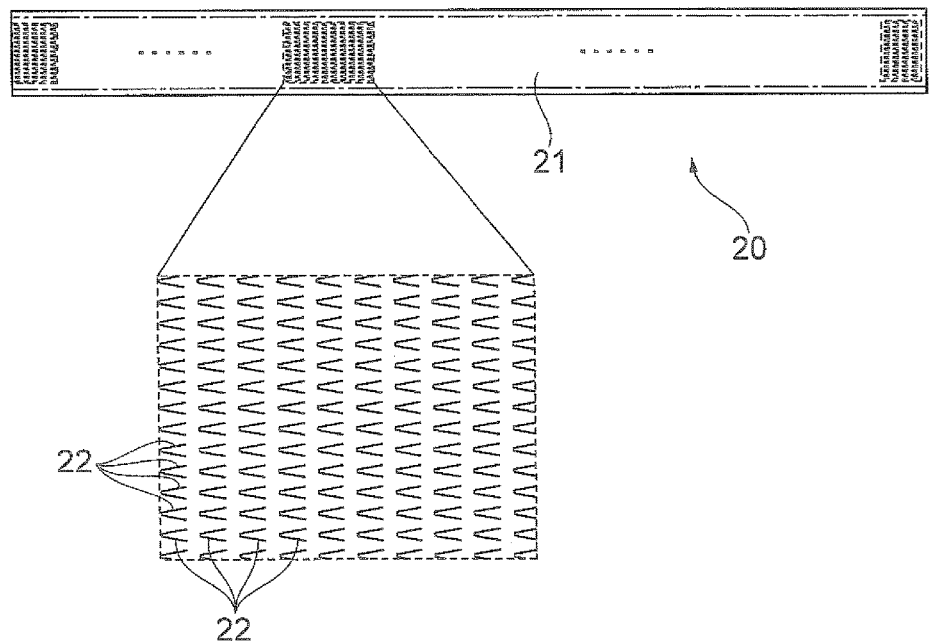
FIG. 1 is a plan view of a microneedle sheet used with an applicator according to an embodiment.
Figure 2:
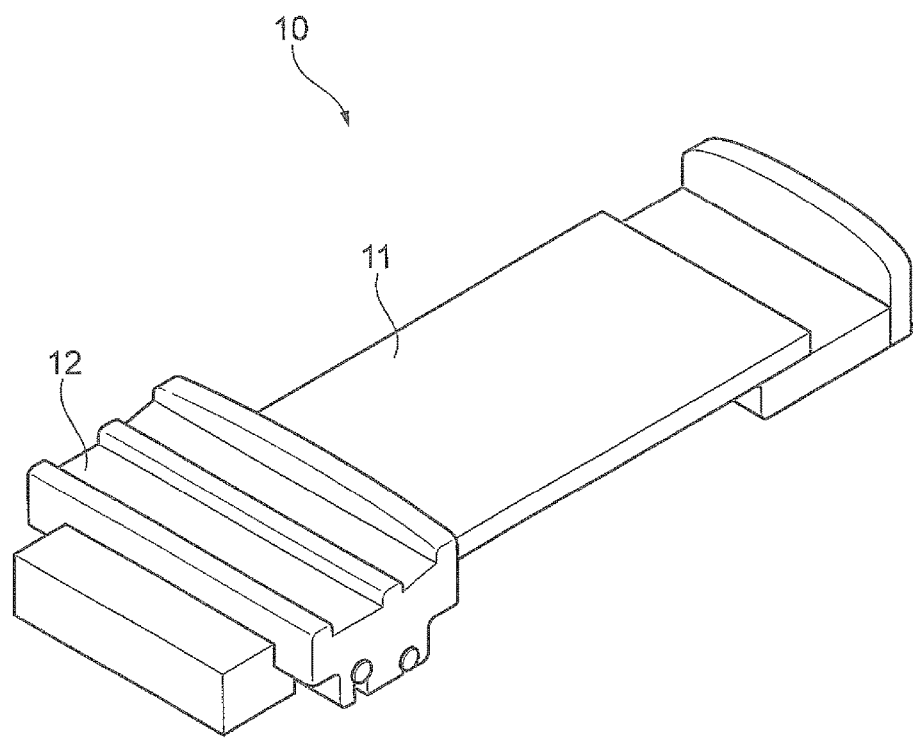
FIG. 2 is a perspective view of the applicator according to a first embodiment.
Figure 3:
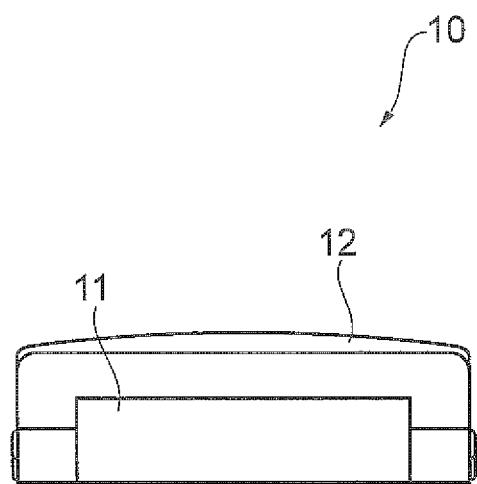
FIG. 3 is a front view corresponding to FIG. 2.
Figure 4:
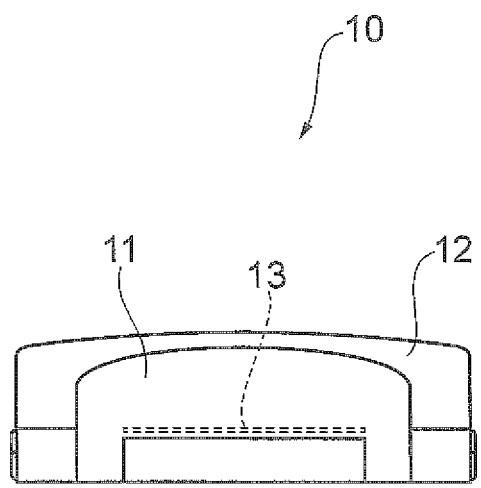
FIG. 4 is a rear view corresponding to FIG. 2.
Figure 5:
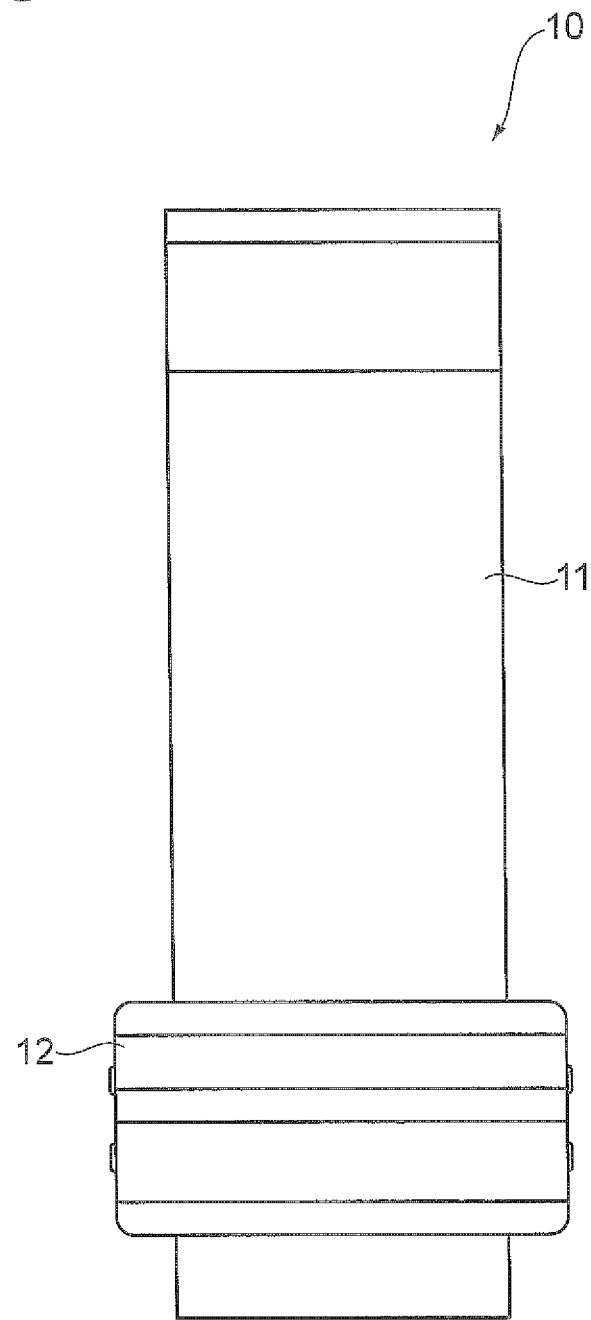
FIG. 5 is a plan view corresponding to FIG. 2.
Figure 6:
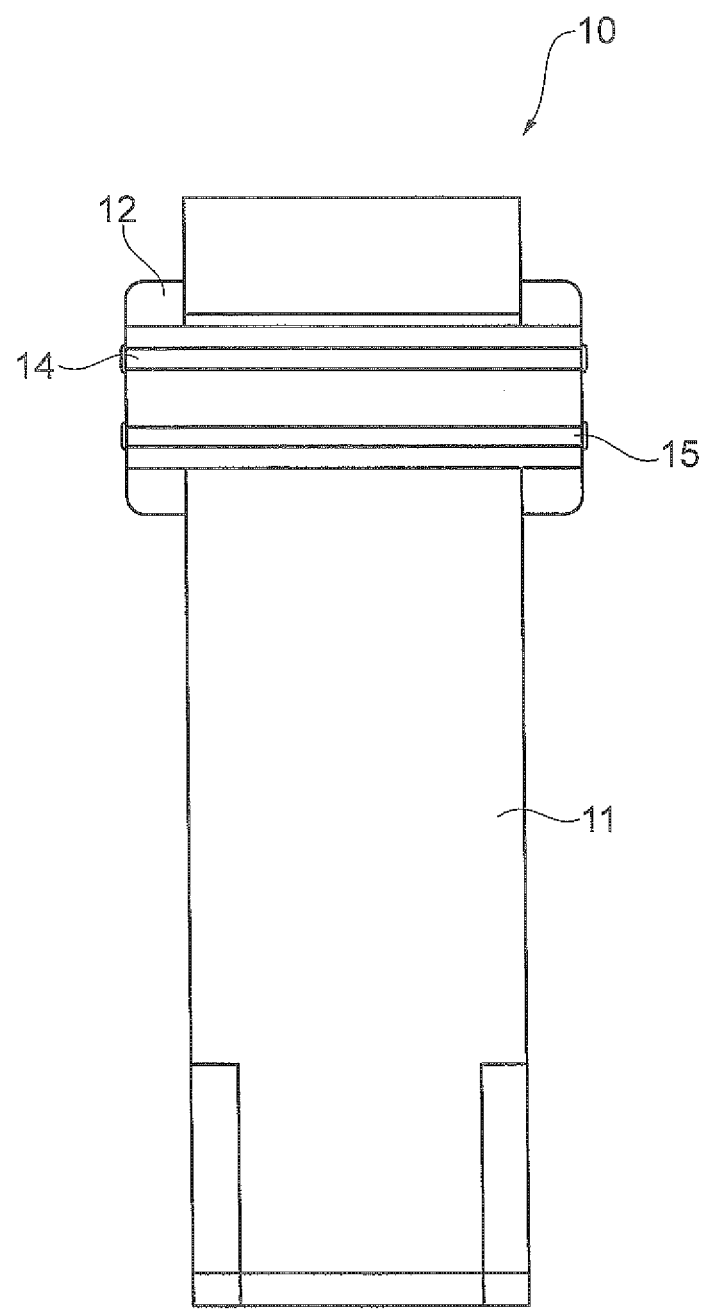
FIG. 6 is a bottom view corresponding to FIG. 2.
Figure 7:
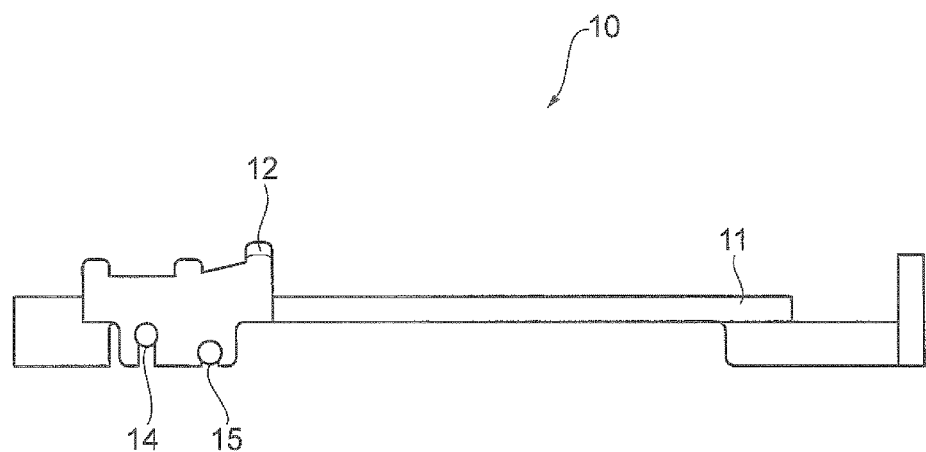
FIG. 7 is a right side view corresponding to FIG. 2.
Figure 8:
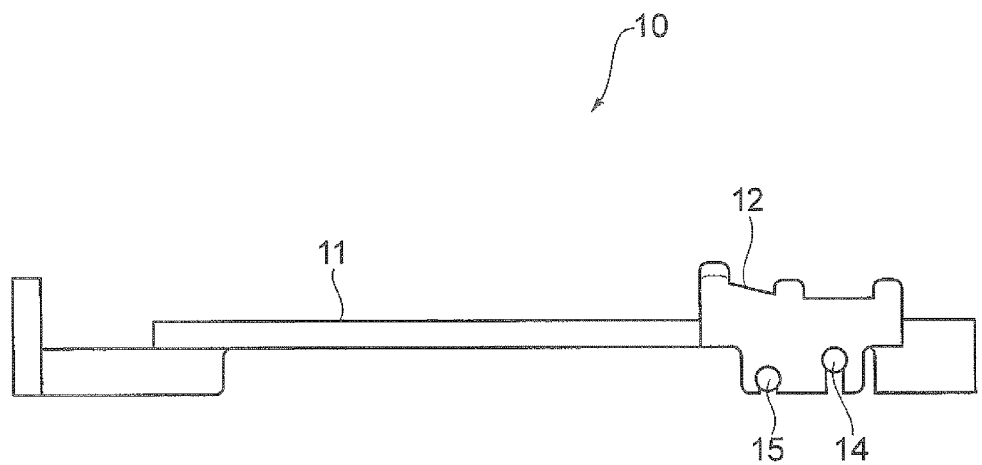
FIG. 8 is a left side view corresponding to FIG. 2.

First, the microneedle sheet 20 attached to the applicator 10 will be described. As shown in FIG. 1, the microneedle sheet 20 is shaped like a strip and has a plurality of microneedles 22 formed on the sheet generally along the main surface 21 of the sheet. These microneedles 22 are arranged in alignment with each of the longitudinal direction and the width direction of the sheet. The tip ends of all of the microneedles 22 are oriented toward one end of the sheet (leftward in FIG. 1) without exception.

The microneedle sheet 20 and the microneedles 22 are of any material. For example, the microneedle sheet 20 and the microneedles 22 may be made from any one of stainless steel, polyethylene terephthalate (PET), other metals, other resins, biodegradable materials, ceramics, and bioabsorbable materials. Alternatively, the microneedle sheet 20 and the microneedles 22 may be made from these materials in combination.

The microneedles 22 can be formed by etching. If the sheet is metallic, the microneedles 22 can be formed by etching the sheet by chemicals. If the sheet is non-metallic, the microneedles 22 can be formed by cutting the sheet by laser. In these cases, a gap is produced on the periphery of the microneedles 22. It is needless to say that the microneedles 22 can be formed by any technique other than etching. Although the microneedles 22 are each triangular in the present embodiment as shown in FIG. 1, the microneedles may have any shape. In any case, the microneedle sheet 20 can be produced readily and inexpensively because there is no need for raising the microneedles 22 from the main surface 21 of the sheet in advance.

The microneedle sheet 20 may be of any size. Specifically, the lower limit of the thickness may be 5 μm or 20 μm, and the upper limit of the thickness may be 1000 μm or 300 μm. The lower limit of the length may be 0.1 cm or 1 cm, and the upper limit of the length may be 50 cm or 20 cm. The lower limit of the width may be 0.1 cm or 1 cm, and the upper limit of the width may be 60 cm or 30 cm. The lower limits of the length and the width of the microneedle sheet 20 are determined considering the dose of active components, and the upper limits of the length and the width may be determined considering the size of the living body.

Parameters pertaining to the microneedles 22 may also have any value. Specifically, the lower limit of the height of each needle may be 10 μm or 100 μm, and the upper limit of the height may be 10000 μm or 1000 μm. The lower limit of the density of needles may be 0.05 needle/cm$^2$ or 1 needle/cm$^2$, and the upper limit of the density may be 10000 needles/cm$^2$ or 5000 needles/cm$^2$. The lower limit of the density is a value obtained in terms of the number of needles and area with which 1 mg of an active component can be administered. The upper limit of the density is a limit value in consideration of the shapes of the needles.

An active component to be applied to skin may be prepared by the following procedures: coating the microneedle sheet 20 per se with an active component in advance; applying an active component on skin before inserting the microneedles 22 into the skin; and inserting the microneedles 22 into skin and thereafter applying an active component on the skin. If the microneedle sheet 20 is coated with an active component in advance, it is preferable to apply a coating liquid having a predetermined viscosity at a thickness as uniform as possible over the entire sheet. Such application can be easily done because the microneedles 22 are arranged along the main surface 21. The coating may be carried out using the principles of screen printing or may be carried out by any other method. If a biodegradable sheet is used, an active component may be included in the sheet per se.

Referring now to FIGS. 2 to 8, a structure of the applicator 10 will be described. The applicator 10 has an elongated shape as a whole and includes a guide plate 11 extending in the longitudinal direction and a slider 12 provided on the guide plate 11. In the present embodiment, the side illustrated in FIG. 3 (front view) is defined as the front side of the applicator 10, and the side illustrated in FIG. 4 (rear view) is defined as the back side of the applicator 10. The side illustrated in FIG. 5 (plan view) is defined as the top side of the applicator 10, and the side illustrated in FIG. 6 (bottom view) is defined as the bottom side of the applicator 10.

Examples of the material of the applicator 10 include plastics such as acrylics. The applicator 10, however, may be made from any material, for example, using a metal or any other resin.

The size of the applicator 10 may be determined in accordance with the size of the microneedle sheet 20. For example, the width (the length in the direction orthogonal to the longitudinal direction) of the applicator 10 may be determined in accordance with the width of the microneedle sheet 20. The entire length (the length along the longitudinal direction) of the applicator 10 may be determined considering the length of the microneedle sheet 20 or the range of application of the microneedle sheet 20 to skin.

The guide plate 11 is an elongated plate-shaped member extending linearly and has a foot at its back end. In order to guide the microneedle sheet 20 to the bottom surface of the guide plate 11, a hole 13 is formed on the back side of the guide plate 11 (see FIG. 4).

The slider 12 is attached to the guide plate 11 so as to be able to move along the longitudinal direction of the guide plate 11. Considering the easiness of slide operation, protrusions and depressions are formed on the top surface of the slider 12. This slider 12 includes two elongated cylindrical members extending along the width direction. The first cylindrical member 14 is provided at a position close to the bottom surface of the guide plate 11. The second cylindrical member 15 is provided at the bottom of the slider 12 (at a position where it nearly abuts on the surface of skin during use of the applicator 10) and at the rear of the first cylindrical member 14. The first cylindrical member 14 may be fixed to the slider 12 so as not to rotate or may be attached to the slider 12 so as to be able to rotate. Similarly, the second cylindrical member 15 may be fixed to the slider 12 so as not to rotate or may be attached to the slider 12 so as to be able to rotate. Both of the first cylindrical member 14 and the second cylindrical member 15 may be fixed to the slider 12 so as not to rotate, or both of them may be attached to the slider 12 so as to be able to rotate. Alternatively, one of the first cylindrical member 14 and the second cylindrical member 15 may be fixed to the slider 12 so as not to rotate and the other may be attached to the slider 12 so as to be able to rotate. The diameters of these two cylindrical members 14 and 15 are set in accordance with the thickness of the microneedle sheet 20 and the length (height) of the microneedles 22 and are each, for example, 1 to 4 mm. Alternatively, the diameters of the two cylindrical members 14 and 15 each may be 0.8 to 4 mm, or may be 0.1 to 4 mm. The diameters of the two cylindrical members 14 and 15 may be the same or may be different from each other.

In the inside of the slider 12, a guide path is formed for allowing the microneedle sheet 20 to pass through from the vicinity of the bottom surface of the guide plate 11 to the surface of skin. Specifically, this guide path extends from the back end of the slider 12 to the first cylindrical member 14 generally horizontally, folds back downward at the first cylindrical member 14, and then extends to the second cylindrical member 15 and folds back downward again at the second cylindrical member 15 to reach the surface of skin. In the present embodiment, the direction in which the microneedle sheet 20 is moved is reversed (changed by approximately 180 degrees) at the first cylindrical member 14, because the position of the lower end of the first cylindrical member 14 and the position of the upper end of the second cylindrical member 15 are almost the same in the height direction. Their heights, however, may be different from each other. For example, if the distance between the first cylindrical member 14 and the second cylindrical member 15 in the height direction is increased, the direction in which the microneedle sheet 20 is moved is changed by less than 180 degrees.

Figure 9:
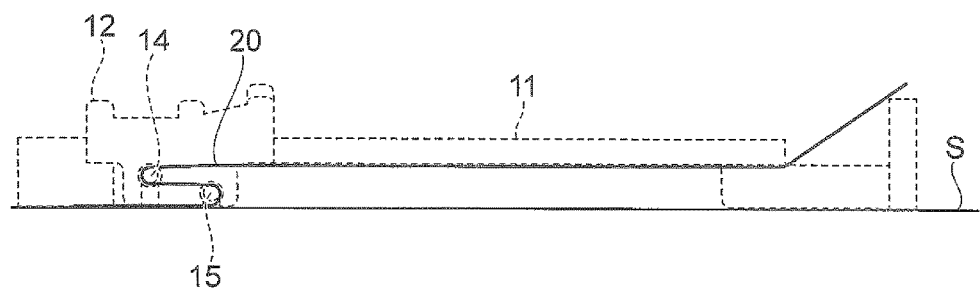
FIG. 9 is a diagram illustrating the microneedle sheet in the first embodiment.
Figure 10:
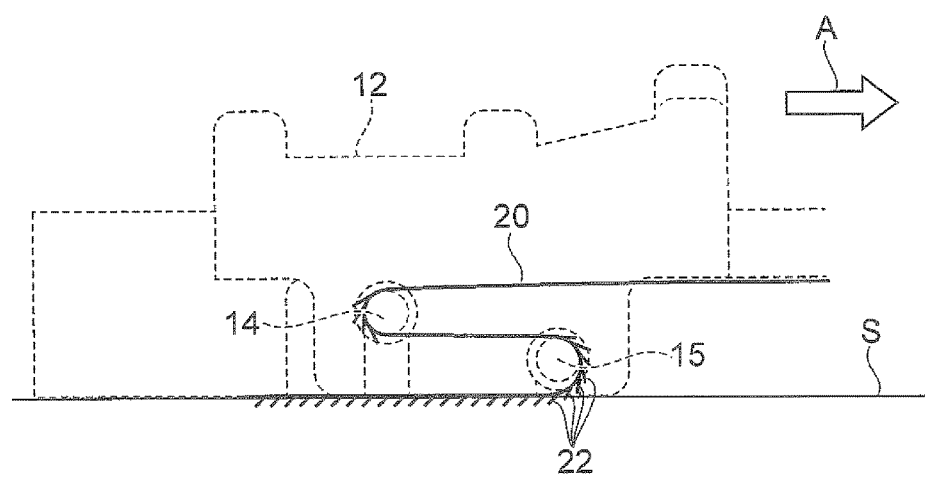
FIG. 10 is a partial enlarged view of FIG. 9.

Referring now to FIGS. 9 to 12, the usage of the applicator 10 and the microneedle sheet 20 will be described. In FIGS. 9 and 10, the microneedle sheet 20 is denoted by a solid line and the applicator 10 is denoted by a broken line in order to facilitate understanding as to how the microneedle sheet 20 is set in the applicator 10.

First, the user sets the microneedle sheet 20 in the applicator 10. Specifically, the user passes the microneedle sheet 20 through the hole 13 and further through the guide path in the slider 12 and then takes out one end of the microneedle sheet 20 to the underside of the second cylindrical member 15. The user then puts the slider 12 on the vicinity of the front end of the guide plate 11 and places the applicator 10 on the skin S such that one end of the microneedle sheet 20 taken out from the guide path faces the front of the applicator 10.

Through a series of these operations, the microneedle sheet 20 is set as shown in FIG. 9. That is, the microneedle sheet 20 passed through the hole 13 is guided along the bottom surface of the guide plate 11 to the slider 12 and is bent into the shape of an S by the two cylindrical members 14 and 15 in the slider 12 to reach the skin S.

In doing so, the user fixes the front end of the microneedle sheet 20 on the skin S with a finger, a adhesive tape, or other means so that the microneedle sheet 20 is not displaced on the skin due to the slide operation described later. Alternatively, the front end of the microneedle sheet 20 may be provided with adhesive for fixing.

After placing the applicator 10 and the microneedle sheet 20 at a place where the active component is to be applied, the user moves the slider 12 toward the back end of the guide plate 11 (in the direction denoted by the arrow A in FIG. 10). This slide operation allows the microneedle sheet 20 to be guided to the second cylindrical member 15 corresponding to the bending portion, and the portion of the microneedle sheet 20 that reaches the second cylindrical member 15 is bent (reversed) at that position. As shown in FIG. 10, the microneedles 22 located at the bent portion are then raised from the main surface 21 of the sheet, and the raised microneedles 22 stick into the skin S.

Figure 11:
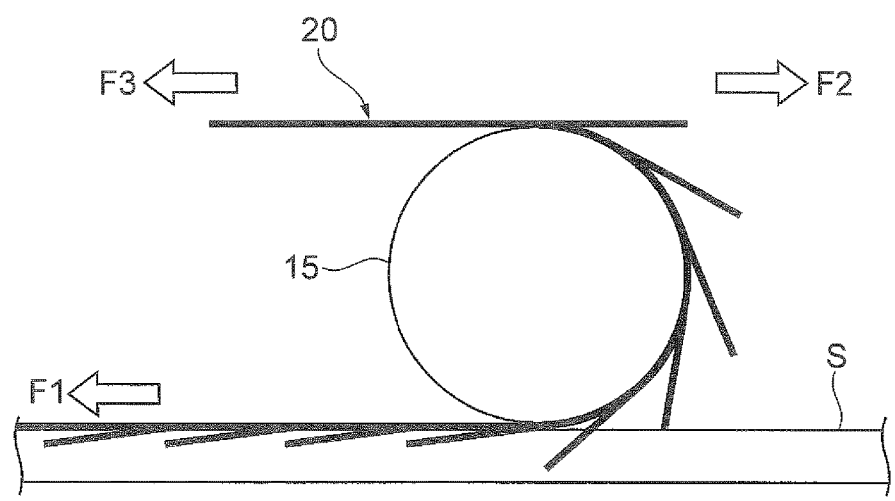
FIG. 11 is a diagram illustrating forces exerted on the microneedle sheet.

The microneedle sheet 20 passes through the first cylindrical member 14 before reaching the second cylindrical member 15. Since the first cylindrical member 14 guides the microneedle sheet 20 to the second cylindrical member 15 by reversing the direction in which the sheet 20 is moved, it can be said that the first cylindrical member 14 applies some resistance against the movement of the microneedle sheet 20. That is, the first cylindrical member 14 corresponds to the resistive portion. The term "resistive portion" as used in the specification of the present application refers to the portion provided for the purpose of removing the slack of the microneedle sheet between the resistive portion and the bending portion (in the present embodiment, the second cylindrical member 15) and applying tension to the bending portion. As described above, when the resistive portion is a cylindrical member, the resistive portion may not rotate or may be rotatable. As shown in FIG. 11, the microneedle sheet 20 is subjected to force F1 exerted on the fixed end (front end) on the skin S, force F2 pulling the slider 12 backward, and force F3 exerted in the direction of the free end (back end) of the microneedle sheet 20. It can be said that force F3 is caused by resistance at the first cylindrical member 14.

A row of the microneedles 22 along the width direction of the microneedle sheet 20 are raised at a time at the second cylindrical member 15. The angle between the raised microneedle 22 and the main surface 21 is greater than 0 degrees and less than 180 degrees, as a matter of course. Although the microneedles 22 are also raised temporarily when passing through the first cylindrical member 14, this does not interfere with the passage of the microneedles 22 through the second cylindrical member 15.

Figure 12:
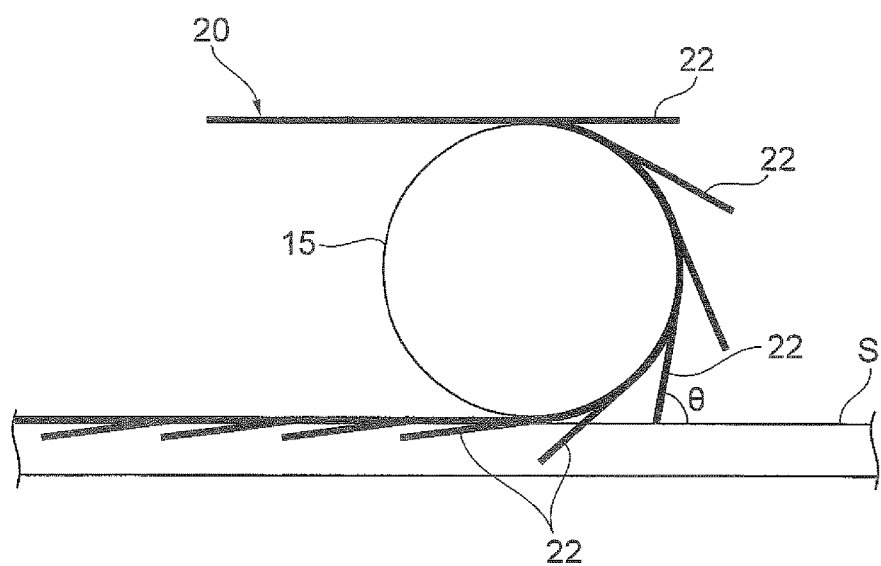
FIG. 12 is a diagram schematically illustrating a manner of puncture.
Figure 13:
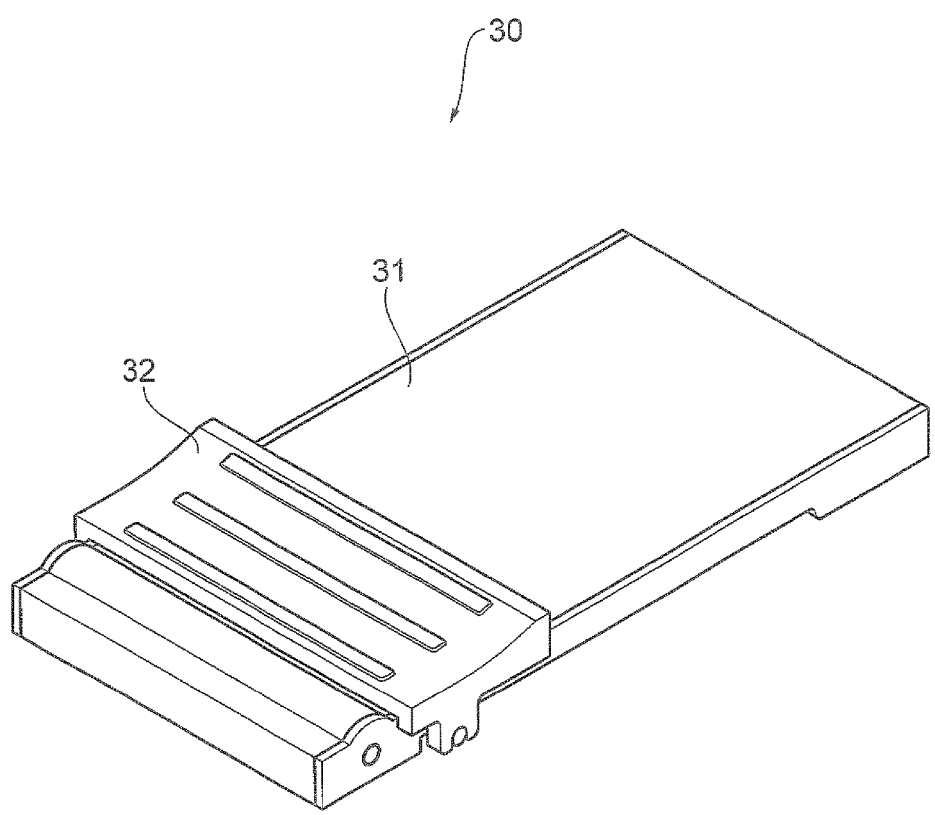
FIG. 13 is a perspective view of an applicator according to a second embodiment.
Figure 14:
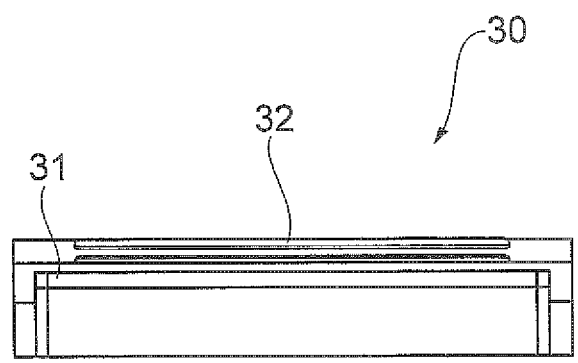
FIG. 14 is a front view corresponding to FIG. 13.
Figure 15:
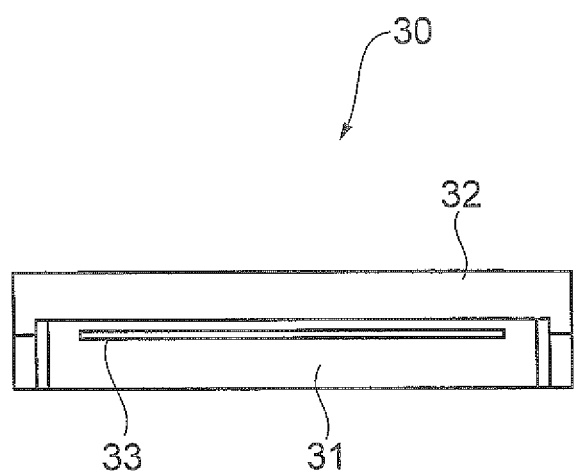
FIG. 15 is a rear view corresponding to FIG. 13.
Figure 16:
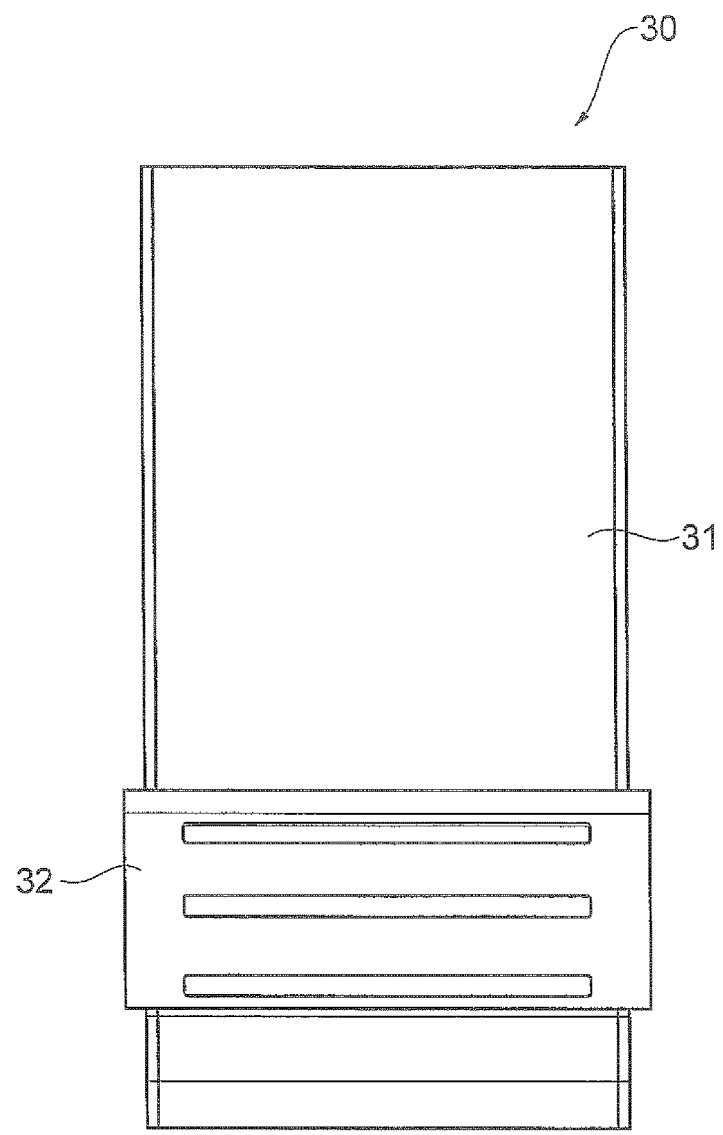
FIG. 16 is a plan view corresponding to FIG. 13.
Figure 17:
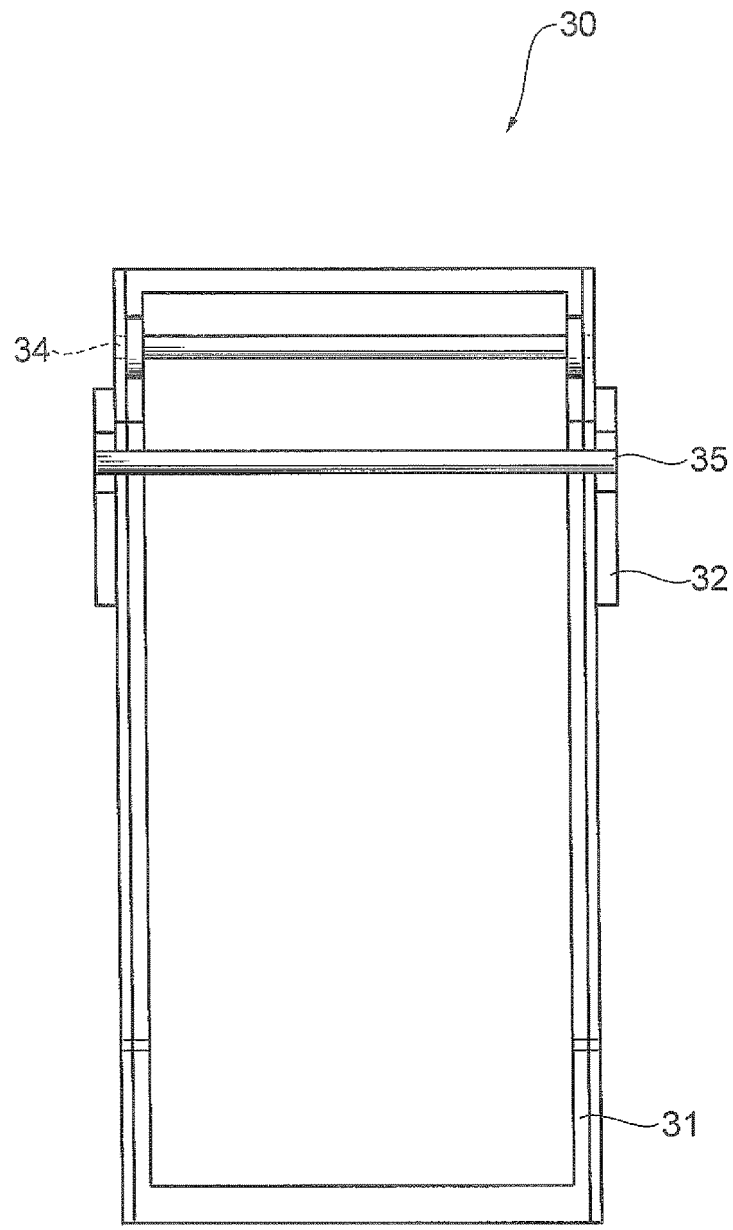
FIG. 17 is a bottom view corresponding to FIG. 13.
Figure 18:
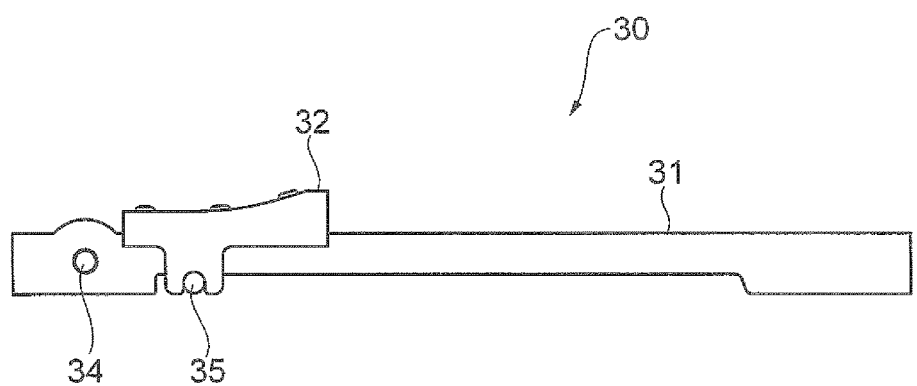
FIG. 18 is a right side view corresponding to FIG. 13.
Figure 19:
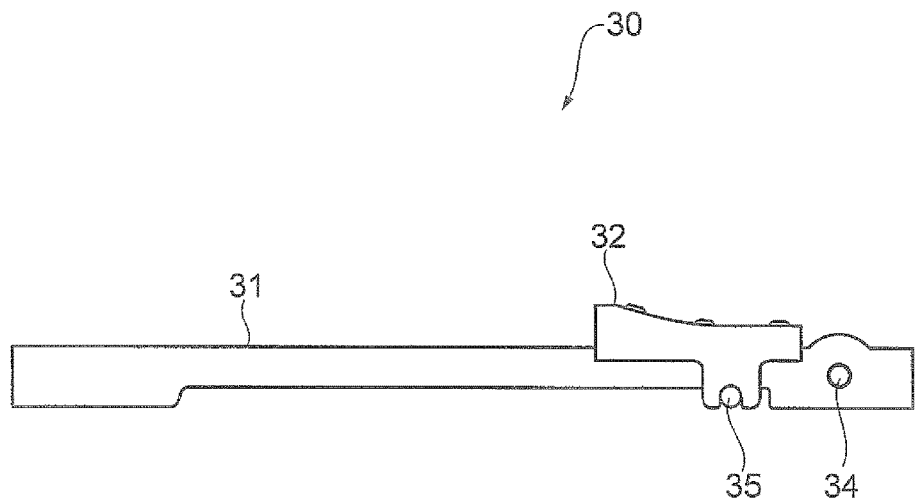
FIG. 19 is a left side view corresponding to FIG. 13.

As shown in FIG. 12, the angle of insertion θ (the angle between the microneedle 22 and the skin S) during insertion of the microneedle 22 raised from the main surface 21 into the skin is also greater than 0 degrees and less than 180 degrees. The lower limit of the angle of insertion may be 20 degrees, 34 degrees, or 40 degrees, and the upper limit of the angle may be 160 degrees, 140 degrees, or 100 degrees.

The user moves the slider 12 by a desired distance, so that a plurality of microneedles 22 in the range of the distance stick into the skin. The user therefore can administer a desired amount of active component by adjusting the area of application of the microneedle sheet 20.

As described above, according to the present embodiment, the first cylindrical member 14 can apply resistance against the movement of the microneedle sheet 20 to stabilize the movement of the microneedle sheet 20. Accordingly, the microneedles 22 subsequently raised by the second cylindrical member 15 can be inserted into skin with a constant force. That is, the reproducibility of puncture can be increased.

In the present embodiment, the employment of two cylindrical members 14 and 15 as the resistive portion and the bending portion, respectively, can simplify the structure of the applicator 10. With the employment of these cylindrical members 14 and 15, the pressure from the cylindrical members does not concentrate on any particular portion of the microneedle sheet 20 when the sheet 20 is deformed, thereby preventing damage to the microneedle sheet 20 more reliably.

In the present embodiment, the first cylindrical member 14 can reverse (change by approximately 180 degrees) the direction in which the microneedle sheet 20 is moved, thereby to apply necessary resistance to the microneedle sheet 20.

The applicator 10 inserts the microneedles 22 into skin by raising the microneedles 22 and pushing the raised microneedles 22 into skin, rather than giving impact to the microneedle sheet 20. Thus, an active component can be administered to the subject without causing a sense of fear.

When it comes to the microneedle sheet 20, the microneedles 22 extend generally along the main surface 21 of the sheet until the first cylindrical member 14 bends the microneedle sheet 20. There is therefore no concern that the microneedles 22 touch or get caught in other objects (for example, the user's skin or clothes) unless the applicator 10 is used. As a result, the security in handling the microneedles 22 can be ensured. For example, the user can safely carry out storage and conveyance of the microneedle sheet 20 or make preparations immediately before use.

Second Embodiment

Referring to FIGS. 13 to 19, a structure of an applicator 30 according to a second embodiment will be described. In the present embodiment, the side illustrated in FIG. 14 (front view) is defined as the front side of the applicator 30, and the side illustrated in FIG. 15 (rear view) is defined as the back side of the applicator 30. The side illustrated in FIG. 16 (plan view) is defined as the top side of the applicator 30, and the side illustrated in FIG. 17 (bottom view) is defined as the bottom side of the applicator 30.

The applicator 30 also has an elongated shape as a whole and includes a guide plate 31 extending in the longitudinal direction and a slider 32 provided on the guide plate 31. The main difference between the applicator 30 and the applicator 10 is that the first cylindrical member is provided not on the slider but on the guide plate. In the following, the configuration different from the first embodiment will be specifically described and the description of the same configuration as in the first embodiment will be omitted.

The guide plate 31 is an elongated plate-shaped member extending linearly. The guide plate 31 has a protrusion at its top front for preventing dropping of the slider 32 described later. A foot is provided on the back end of the guide plate 31. A first cylindrical member 34 is attached in the vicinity of the protrusion. In order to guide the microneedle sheet 20 to the first cylindrical member 34, the guide plate 31 has a hole 33 on its back end and a guide path extending from the hole 33 to the first cylindrical member 34.

The slider 32 is attached to the guide plate 31 such that it can move along the longitudinal direction of the guide plate 31. Considering the easiness of slide operation, protrusions and depressions are formed on the top surface of the slider 32. A second cylindrical member 35 is provided at the bottom of the slider 32 (at a position where it nearly abuts on the surface of skin during use of the applicator 30). In the inside of the slider 32, a guide path is formed to guide the microneedle sheet 20 folded by the first cylindrical member 34 to the surface of skin via the second cylindrical member 35.

The manner in which the first cylindrical member 34 and the second cylindrical member 35 are attached (whether they are fixed so as not to rotate or attached so as to be able to rotate) may be determined as desired in the same manner as the first cylindrical member 14 and the second cylindrical member 15 in the first embodiment. The diameters of the two cylindrical members 34 and 35 may also be determined in the same manner as in the first embodiment.

Figure 20:
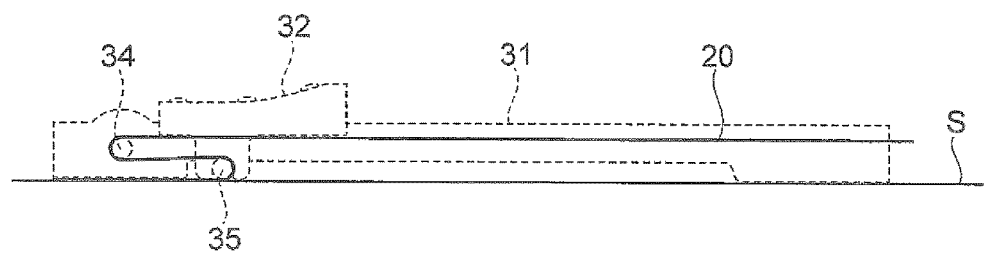
FIG. 20 is a diagram illustrating the microneedle sheet in the second embodiment.
Figure 21:
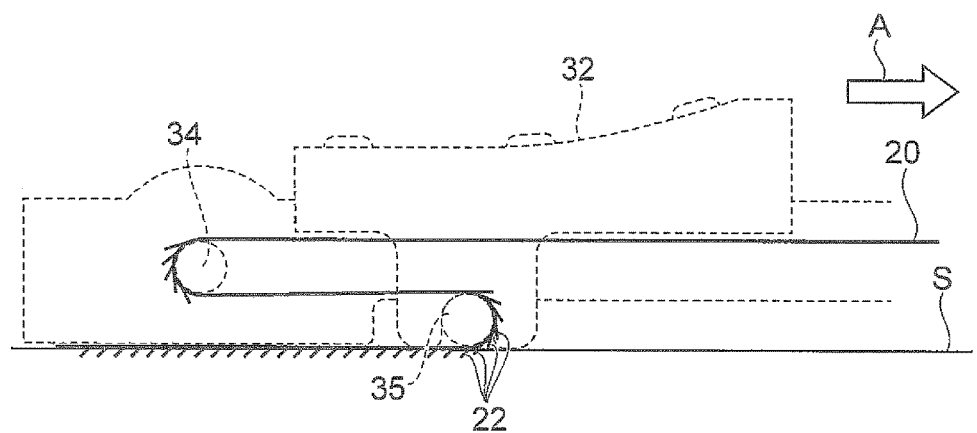
FIG. 21 is a partial enlarged view of FIG. 20.

Referring now to FIGS. 20 and 21, the usage of the applicator 30 and the microneedle sheet 20 will be described. In FIGS. 20 and 21, the microneedle sheet 20 is denoted by a solid line and the applicator 30 is denoted by a broken line in order to facilitate understanding as to how the microneedle sheet 20 is set in the applicator 30.

First, the user sets the microneedle sheet 20 in the applicator 30. Specifically, the user passes the microneedle sheet 20 through the hole 33 to the guide path in the guide plate 31, then folds back the microneedle sheet 20 at the first cylindrical member 34 to allow the microneedle sheet 20 to pass through the guide path in the slider 32, and then finally takes out the microneedle sheet 20 to the underside of the second cylindrical member 35. The user then puts the slider 32 on the vicinity of the front end of the guide plate 31 and places the applicator 30 on the skin S such that one end of the microneedle sheet 20 taken out from the guide path faces the front side of the applicator 30, as shown in FIG. 20.

Through a series of these operations, the microneedle sheet 20 is set as shown in FIG. 20. That is, the microneedle sheet 20 passed through the inside of the guide plate 31 is guided to the first cylindrical member 34 and then bent into the shape of an S by the two cylindrical members 34 and 35 to reach the skin S. The front end of the microneedle sheet 20 is fixed to the skin in the same manner as in the first embodiment.

After placing the applicator 30 and the microneedle sheet 20 at a place where an active component is to be applied, the user moves the slider 32 toward the back end of the guide plate 31 (in the direction denoted by the arrow A in FIG. 21). This slide operation allows the microneedle sheet 20 to be guided to the second cylindrical member 35 corresponding to the bending portion, and the portion of the microneedle sheet 20 that reaches the second cylindrical member 35 is bent (reversed) at that portion. As shown in FIG. 21, the microneedles 22 located at the bent portion are then raised from the main surface 21 of the sheet, and the raised microneedles 22 stick into the skin S.

The microneedle sheet 20 passes through the first cylindrical member 34 before reaching the second cylindrical member 35. Since the first cylindrical member 34 guides the microneedle sheet 20 to the second cylindrical member 35 by reversing the direction in which the sheet 20 is moved, it can be said that the first cylindrical member 34 applies some resistance against the movement of the microneedle sheet 20. That is, the first cylindrical member 34 corresponds to the resistive portion. The forces exerted on the microneedle sheet 20 are the same as those in the first embodiment (see FIG. 11).

The present embodiment differs from the first embodiment in that the slide operation allows the second cylindrical member 35 to move away from the first cylindrical member 34, but the manner of insertion of the microneedles 22 is the same as that in the first embodiment. Also in the present embodiment, the user can administer a desired amount of active component by adjusting the area of application of the microneedle sheet 20.

The second embodiment as described above can also achieve the same effects as that in the first embodiment. That is, the first cylindrical member 34 applies resistance against the movement of the microneedle sheet 20 to stabilize the movement of the microneedle sheet 20. Thus, the microneedles 22 subsequently raised by the second cylindrical member 35 can be inserted into skin with a constant force. The reproducibility of puncture is thus increased. The employment of two cylindrical members 34 and 35 can simplify the structure of the applicator 30 and can prevent or minimize damage to the microneedle sheet 20 when it is deformed. The first cylindrical member 34 can reverse the direction in which the microneedle sheet 20 is moved, thereby to apply necessary resistance to the microneedle sheet 20.

In the present embodiment, the first cylindrical member 34 is provided in the guide plate 31. With this configuration, the second cylindrical member 35 moves away from the first cylindrical member 34 through slide operation, and the force necessary for sliding changes according to the distance between the two cylindrical members 34 and 35. Moreover, the microneedle sheet 20 between the two cylindrical members 34 and 35 is wasted. By contrast, in the first embodiment, the distance between the two cylindrical members 14 and 15 does not change, so that the user can move the slider 12 with a constant force and a waste of the microneedle sheet 20 can be minimized.

The present invention has been described above based on the embodiments. The present invention, however, is not intended to be limited to the foregoing embodiments. The present invention is susceptible to various modifications without departing from the gist of the invention.

Although a cylindrical member is used as the resistive portion in the foregoing embodiments, the resistive portion is not intended to be limited to this. For example, a structure that sandwiches the microneedle sheet to such a degree that the sheet can pass through may be employed as the resistive portion. An example of such a structure may be a slit-shaped through hole having upper and lower surfaces of the microneedle sheet come into contact with the inner wall of the through hole during passage of the sheet. Alternatively, a tubular structure (for example, reel) wrapped with the microneedle sheet in advance to feed the microneedle sheet to the bending portion may be employed as the resistive portion.

Although a cylindrical member is used as the bending portion in the foregoing embodiments, the bending portion may have any configuration as long as it can bend the microneedle sheet to raise the microneedles.

A single applicator may include a plurality of resistive portions. Individual resistive portions may have the same or similar structure or may have different structures. For example, all of the resistive portions may be one of the cylindrical member, the slit-shaped through hole, and the tubular structure. Alternatively, the applicator may include at least two of the cylindrical member, the slit-shaped through hole, and the tubular structure, as resistive portions.

If the force applied by the resistive portion against the movement of the microneedle sheet is too strong, the applicator fails in operation (for example, the sliders 12, 32 in the forgoing embodiments fail to move). By contrast, if the resistance applied is too weak, the microneedle sheet fails to be stretched between the resistive portion and the bending portion without slack in the microneedle sheet, and the microneedles are not fully raised. The resistive portion of the applicator is thus designed or produced such that the microneedle sheet is stretched without slack and the user can easily operate the applicator.

REFERENCE SIGNS LIST

10 . . . applicator, 11 . . . guide plate, 12 . . . slider, 14 . . . first cylindrical member (resistive portion), 15 . . . second cylindrical member (bending portion), 20 . . . microneedle sheet, 21 . . . main surface, 22 . . . microneedle, 30 . . . applicator, 31 . . . guide plate, 32 . . . slider, 34 . . . first cylindrical member (resistive portion), 35 . . . second cylindrical member (bending portion).

The invention claimed is:

1. An applicator for applying a plurality of microneedles to skin comprising:
    a first cylindrical member being a resistive portion configured to apply resistance against movement of a microneedle sheet having the plurality of microneedles formed along a main surface of the sheet, each of the plurality of microneedles having a tip and each tip facing toward a first end of the sheet in the longitudinal direction; and
    a second cylindrical member being a bending portion configured to bend the microneedle sheet passed through the resistive portion to change an angle between the plurality of microneedles and the main surface, and thereby raise the plurality of microneedles from the main surface.

2. The applicator according to claim 1, wherein the first cylindrical member is further configured to change the direction of movement of the microneedle sheet.

3. The applicator according to claim 2, wherein the first cylindrical member reverses the direction of movement of the microneedle sheet.

4. The applicator according to claim 2, wherein the second cylindrical member is further configured to bend the microneedle sheet by changing the direction of movement of the microneedle sheet.

5. The applicator according to claim 4, wherein the second cylindrical member reverses the direction of movement of the microneedle sheet.

6. The applicator according to claim 4, further comprising a slider configured to slide the second cylindrical member such that the second cylindrical member moves away from the first cylindrical member.

7. The applicator according to claim 4, further comprising a slider configured to slide the first and second cylindrical members simultaneously.

8. The applicator according to claim 1, wherein the resistive portion sandwiches the microneedle sheet to apply resistance to the microneedle sheet.

9. The applicator according to claim 1, wherein the resistive portion is a tubular structure wrapped with the microneedle sheet to feed the microneedle sheet toward the bending portion.

* * * * *